United States Patent
Fuchs et al.

(10) Patent No.: US 11,304,875 B2
(45) Date of Patent: Apr. 19, 2022

(54) PIERCING PART FOR A MEDICAL INFUSION SYSTEM

(71) Applicant: B. BRAUN MELSUNGEN AG, Melsungen (DE)

(72) Inventors: Jürgen Fuchs, Bad Emstal (DE); Christof Schlitt, Obergrenzebach (DE); Siegbert Vial, Burgwald (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 394 days.

(21) Appl. No.: 15/935,889

(22) Filed: Mar. 26, 2018

(65) Prior Publication Data
US 2018/0280237 A1 Oct. 4, 2018

(30) Foreign Application Priority Data
Mar. 28, 2017 (DE) ...................... 10 2017 205 250.3

(51) Int. Cl.
*A61J 1/20* (2006.01)
*A61M 5/14* (2006.01)

(52) U.S. Cl.
CPC ............. *A61J 1/201* (2015.05); *A61J 1/2075* (2015.05); *A61J 1/2082* (2015.05); *A61M 5/1411* (2013.01)

(58) Field of Classification Search
CPC ........ A61J 1/201; A61J 1/2075; A61J 1/2082; A61J 1/2003; A61J 1/2006; A61J 1/5058;
(Continued)

(56) References Cited

U.S. PATENT DOCUMENTS 3,993,068 A * 11/1976 Forberg ................ A61M 5/162
604/251
4,055,176 A 10/1977 Lundquist
(Continued)

FOREIGN PATENT DOCUMENTS

EP 0582038 A2 2/1994
EP 1747787 A1 1/2007

OTHER PUBLICATIONS

European Search Report for European Application No. 18161304.3, dated Jun. 6, 2018 with partial translation, 12 pages.
(Continued)

*Primary Examiner* — Tatyana Zalukaeva
*Assistant Examiner* — Meagan Ngo
(74) *Attorney, Agent, or Firm* — Culhane Meadows PLLC; Christopher A. Rothe

(57) ABSTRACT

A piercing part for a medical infusion system includes a housing with a piercing mandrel, a fluid channel and a ventilation channel with a first channel portion extending at least substantially parallel to the fluid channel and with a second channel portion diverted towards an outside of the housing and to which an air filter element and a fluid shut-off member are assigned. A drip chamber can include a piercing part. The piercing part can be produced by an injection molding tool. The second channel portion in the housing is oriented parallel to the first channel portion and open towards an inside of the housing. An open region of the channel portion is closed by a separately produced closure part. The piercing part can be used with a medical infusion system.

11 Claims, 2 Drawing Sheets

Figure 1:
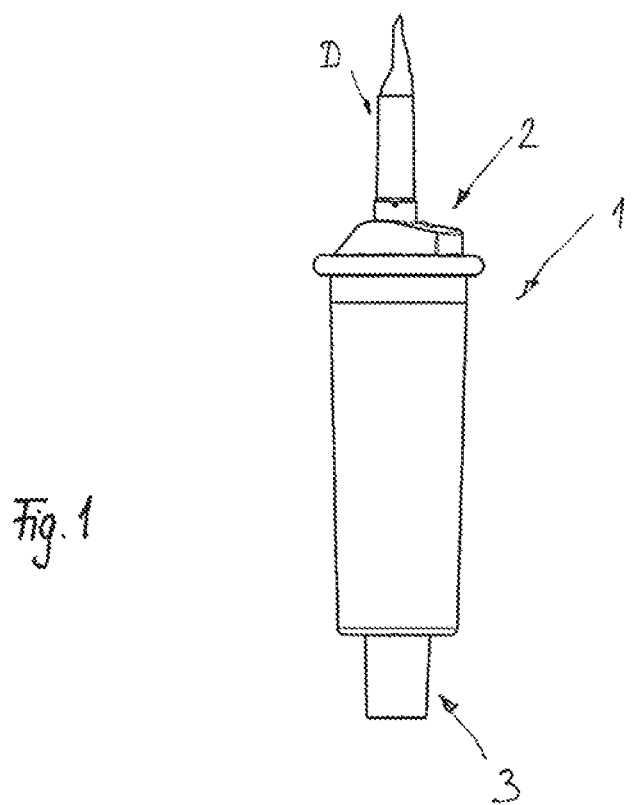

(58) Field of Classification Search
CPC ...... A61J 1/2062; A61J 1/2068; A61J 1/2072; A61M 5/1411; A61M 5/162; A61M 5/38; A61M 2205/7536; A61M 2207/10; A61M 5/16804; A61M 5/1689; A61M 5/40; A61M 1/3627; A61M 2005/1623; B29C 45/26

See application file for complete search history.

(56) References Cited

U.S. PATENT DOCUMENTS

| | | | | |
|---|---|---|---|---|
| 4,842,588 | A * | 6/1989 | Jones | A61M 5/1411 604/126 |
| 5,098,408 | A * | 3/1992 | Tarzian | A61M 5/16881 251/125 |
| 5,242,424 | A * | 9/1993 | Chen | A61M 5/1411 604/122 |
| 5,779,674 | A * | 7/1998 | Ford | A61M 5/38 604/122 |
| 2004/0073189 | A1 * | 4/2004 | Wyatt | A61M 5/162 604/411 |
| 2005/0201418 | A1 * | 9/2005 | Aoyama | A63B 37/0003 370/480 |
| 2007/0043325 | A1 | 2/2007 | Guala | |
| 2011/0275988 | A1 | 11/2011 | Davis et al. | |
| 2013/0144248 | A1 * | 6/2013 | Putter | A61J 1/2096 604/405 |
| 2016/0331893 | A1 * | 11/2016 | Yeh | A61M 39/24 |
| 2017/0340812 | A1 * | 11/2017 | Berg | A61M 5/1411 |

OTHER PUBLICATIONS

German Search Report for German Application No. 10 2017 205 250.3, dated Jan. 15, 2018 with partial translation, 7 pages.

* cited by examiner

PIERCING PART FOR A MEDICAL INFUSION SYSTEM

RELATED APPLICATION(S)

This application claims the benefit of priority of German patent application no. DE 10 2017 205 250.3, filed Mar. 28, 2017, the content of which is incorporated by reference in its entirety into this application.

FIELD

The present disclosure relates to a piercing part for a medical infusion system, with a housing which has a piercing mandrel and which has a fluid channel and also a ventilation channel with a first channel portion extending at least substantially parallel to the fluid channel and with a second channel portion which is diverted towards an outside of the housing and to which an air filter element and a fluid shut-off member are assigned. The present disclosure furthermore relates to a drip chamber for a medical infusion system with such a piercing part, and to an injection molding tool for producing the housing of the piercing part.

BACKGROUND

A piercing part of this kind is known from EP 0 582 038 B1. The known piercing part is part of a drip chamber of a medical infusion system. The piercing part has a housing which comprises a piercing mandrel. Extending in the region of the piercing mandrel are a fluid channel and also a first channel portion of a ventilation channel extending parallel to the fluid channel. The first channel portion merges by way of a diversion into a second channel portion, which is open towards an outside of the housing. The second channel portion is diverted through 90° relative to the first channel portion. An air filter element and a fluid shut-off member in the form of a non-return valve are integrated in the second channel portion open towards the outside. The housing of the piercing part is produced in one piece in a plastic injection molding process. To obtain the second channel portion diverted through 90° relative to the first channel portion, the use of a slide in the injection molding tool is necessary.

SUMMARY

An object of this disclosure is to make available a piercing part, a drip chamber and an injection molding tool which are of the type mentioned above and which permit simpler production.

As regards the piercing part, this object is achieved by the fact that the second channel portion in the housing is oriented parallel to the first channel portion and is open towards an inside of the housing, and that the open region of the channel portion is closed by a separately produced closure part. By virtue of the fact that the second channel portion is not oriented transversely with respect to the first channel portion, as in the prior art, but instead parallel to the first channel portion, it is possible, in the case of production in an injection molding tool, to demold the housing without using slides. Accordingly, in the state when the piercing part is ready to function, both the piercing mandrel and the second channel portion of the ventilation channel are oriented vertically. For the production of the housing, an injection molding tool can accordingly have two tool halves, which can easily be demolded in mutually opposite directions. An injection mold of the injection molding tool accordingly has only a single demolding direction. The additional, separately produced closure part ensures that, when the piercing part is in the state ready to function, the second channel portion is closed off from an inside of the housing. The closure part preferably provides a 180° diversion. It is only when the closure part is fitted that the second channel portion of the ventilation channel is able to function. The production of the piercing part according to the present disclosure in an injection molding process is considerably more economical than the production of a known piercing part. The piercing part is advantageously a component part of a drip chamber of a medical infusion system, wherein the housing of the piercing part preferably forms an upper end region of the drip chamber. The housing is advantageously connected rigidly to a transparent hollow cylinder of the drip chamber.

In one embodiment, the second channel portion has a channel outlet to the outside of the housing, which channel outlet is oriented parallel to the first channel portion of the ventilation channel. Advantageously, the entire second channel portion, including its channel outlet, is parallel to the first channel portion, preferably laterally offset towards the outside from the first channel portion in relation to a central longitudinal axis of the housing. The separately produced closure part advantageously produces a 180° diversion of an air flow or fluid flow for the second channel portion.

In a further embodiment, the fluid shut-off member is designed as a non-return valve. The non-return valve is designed in such a way that the non-return valve is able to open in the flow direction towards the first channel portion. In this way, air can pass from the outside of the housing into the second channel portion and from there into the first channel portion of the ventilation channel. At the same time, any liquid flowing in the opposite direction through the first channel portion towards the second channel portion is held back by the non-return valve. Contamination of the air filter element is thus reliably avoided.

In a further embodiment, the non-return valve is designed as a bell-like membrane body made of an elastomer material. The bell-like membrane body is advantageously oriented like a beaker towards the channel outlet to the outside of the housing and has, in its bottom region, a slit which can open in the flow direction towards the first channel portion and is tightly closed in the flow direction towards the outside of the housing.

In a further embodiment, the closure part forms a 180° diversion between the first channel portion and the second channel portion. The closure part defines a wall of the second channel portion through which a corresponding flow diversion of an air stream or of a fluid stream is effected between the two mutually parallel channel portions of the ventilation channel.

In a further embodiment, the closure part is designed as a stopper positioned with force-fit engagement in a seat of the housing. The stopper is closed towards an inside of the housing and forms a wall of the second channel portion, such that the stopper seals off the second channel portion from the inside of the housing.

In a further embodiment, the housing, including the piercing mandrel and the channel portions of the ventilation channel, is produced in one piece from a thermoplastic material in an injection molding process. A corresponding injection mold for producing the housing has only a single demolding direction.

In a further embodiment, the fluid shut-off member is designed as a hydrophobic or oleophobic membrane. This ensures that the fluid shut-off member holds back fluids, in particular water-containing or oil-containing fluid substances. At the same time, however, the membrane is designed such that air can pass through the membrane.

As regards the drip chamber, the object is achieved by the features of drip chambers described herein.

The present disclosure further relates to an injection molding tool for producing a housing for a piercing part as described above. For the production of the housing, according to the present disclosure, two slide-free tool halves are provided which can be demolded towards opposite sides. The injection molding tool accordingly has two mold halves, which are sufficient for the production of the housing by injection molding and which can be demolded relative to each other in a single demolding direction in order to free the finished housing of the piercing part.

BRIEF DESCRIPTION OF THE DRAWING FIGURE(S)

Further advantages and features will become clear from the following description of a preferred illustrative embodiment shown in the drawings.

Figure 2:
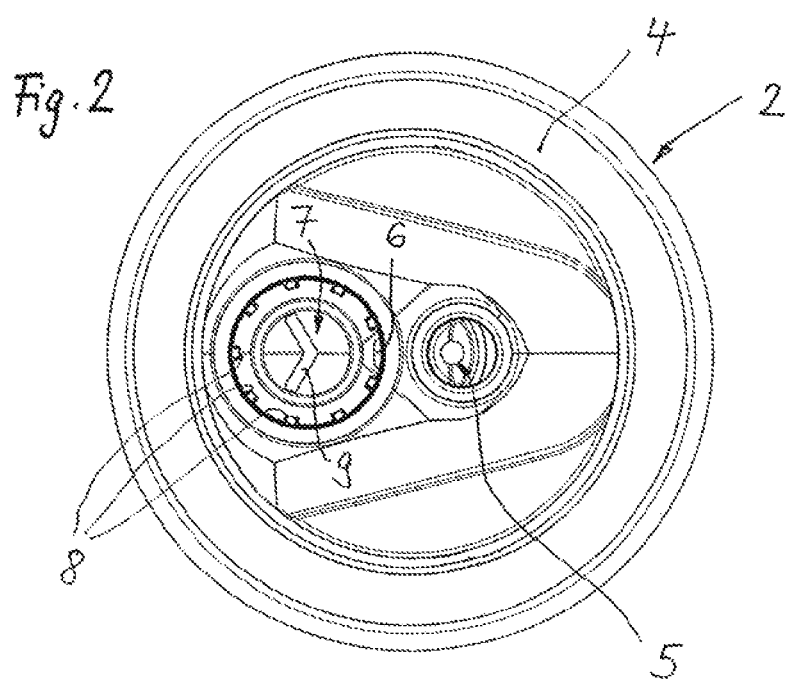
Figure 3:
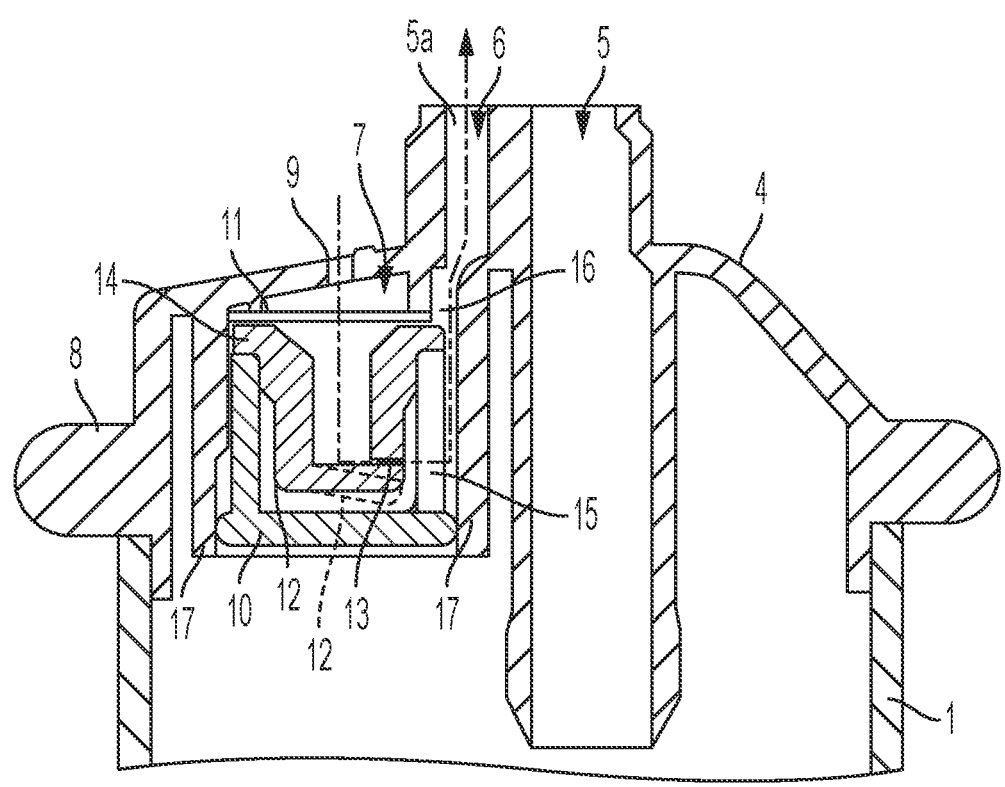

FIG. 1 shows an embodiment of a drip chamber according to the present disclosure, with an embodiment of a piercing part according to the present disclosure in the region of an upper face of the drip chamber, FIG. 2 shows an enlarged view of the piercing part according to FIG. 1 from below, and FIG. 3 shows an enlarged longitudinal section through the piercing part according to FIG. 2.

DETAILED DESCRIPTION

A drip chamber 1 of a medical infusion system is oriented vertically in a functional state and has a piercing part 2 in the region of its upper face. In the region of a lower face, an attachment region 3 is provided for attachment to a hose line system of the medical infusion system. The piercing part 2 has a housing 4 which is produced in one piece from a thermoplastic material in an injection molding process. In the region of its lower face, the housing 4 is fitted by means of a flange onto a hollow-cylindrical front end region of the drip chamber 1 and is rigidly connected to said front end region in particular by adhesion or by welding.

The piercing part 2 has a piercing mandrel D which, according to FIGS. 2 and 3, is provided with a fluid channel 5 and with a ventilation channel 5a. Both the fluid channel 5 and the ventilation channel 5a are integral component parts of the housing 4 of the piercing part 2. The piercing mandrel D is also an integral component part of the housing 4. In a vertical orientation of the piercing mandrel D, the fluid channel 5 likewise extends vertically. The fluid channel 5 is open towards a tip of the piercing mandrel D and towards an inside of the drip chamber 1.

Parallel to and alongside the fluid channel 5, a first channel portion 6 of the ventilation channel 5a extends in the piercing mandrel D. In a vertical orientation of the piercing mandrel D, the first channel portion 6 is likewise oriented vertically and is open in the region of a tip of the piercing mandrel D. The first channel portion 6 is additionally open towards a second channel portion 7 of the ventilation channel, which second channel portion 7 is positioned in the housing 4 parallel to and alongside the first channel portion 6 under the piercing mandrel D. At a transition of the piercing mandrel D into a widened housing portion of the housing 4, the first channel portion 6 of the ventilation channel merges in an open manner into the second channel portion 7, wherein the second channel portion 7 has a much larger free cross section than the first channel 5 portion 6. The second channel portion 7 has a pot-like shape which is open towards the inside of the housing 4 and which is delimited by a peripheral cylindrical wall 17. In a vertical orientation of the piercing mandrel D, the second channel portion 7 is likewise oriented vertically, specifically in a position laterally off set from the first channel portion 6. In the region of its upper face, the second channel portion 7 is provided with a channel outlet 9 to the outside of the housing 4, which channel outlet 9 is shaped like an arrow (FIG. 2). The peripheral cylindrical wall 17, which radially delimits the second channel portion 7, is provided radially on the inside with support ribs 8, which are distributed about the circumference of the cylindrical wall 17.

In the region of a wall of the housing 4, the second channel portion 7 has a peripheral support flange (not shown in any detail) which surrounds the channel outlet 9 internally and which is provided to support a disc-shaped air filter element 11.

The air filter element 11 is adjoined internally by a bell-shaped membrane body 12, which is produced from an elastomer material. In the region of its upper face (in relation to the view in FIG. 3), the membrane body 12 has a peripheral support flange 14, which extends radially outwards in relation to a beaker-like wall of the bell-shaped membrane body 12. This support flange 14 is pressed by a closure part, in the form of a stopper 10, against the air filter element 11 in the region of the annular flange of the housing 4. The stopper 10 forms a lid for closing off and sealing the channel portion 7 in the region of the inner wall of the housing-side cylindrical wall 17. The stopper 10 has a peripheral annular wall which is clamped with force-fit engagement onto the support ribs 8. The peripheral annular wall of the stopper 10 is provided with a slit 15 which is open radially over an entire height of the annular wall of the stopper 10, in order to establish an opening of the second channel portion 7 to the first channel portion 6.

The stopper 10 is designed in such a way that it completely seals off the second channel portion 7 from the inside of the housing. For this purpose, the lid of the stopper 10 has a peripheral edge region which bears tightly and with force-fit engagement on the peripheral cylindrical wall 17 of the housing 4. In addition to the force-fit sealing action, the stopper 10 can also be connected to the wall 17 by cohesive bonding, in particular by adhesion or by welding.

In the region of its lower face, the bell-shaped membrane body 12 serving as non-return valve has a closed bottom, which defines a beaker shape for a lower half of the bell-shaped membrane body 12. The closed bottom can be folded down in a pressure-dependent manner by means of a slit 13 which is provided in the membrane body 12 in a radial plane laterally above the bottom, as a result of which a passage from the interior of the membrane body 12 towards the radial slit 15 is freed (to the right in the drawing). The slit 13 extends horizontally over a large part of the circumference of the membrane body 12, such that the unslit, remaining wall region of the membrane body 12 forms a hinge in the form of a flexure bearing. An open position of the bottom is indicated by broken lines. The slit 13 allows the elastically deformable bottom of the membrane body 12 to pivot in the closed position towards an inside of the lid of the stopper 10, wherein the bottom of the membrane body 12 is spaced apart from the inside of the lid of the stopper 10. During the operation of the piercing part 2, when the piercing mandrel D is pushed into an underside of a fluid storage receptacle, it is thus possible, by corresponding pressure differences between an interior of the fluid storage receptacle and an environment, to obtain an air flow, as indicated by the dot-and-dash arrow in FIG. 3, from the outside of the housing 4 through the channel outlet 9, through the air filter element 11 and through the slit 13 radially to the bottom of the membrane body 12, wherein the air stream indicated by the dot-and-dash line is then diverted via the inside of the lid of the stopper 10 towards the radial slit 15 and is rotated by the latter through 180° and guided upwards along the inside of the annular wall 17 to the first channel portion 6. A desired ventilation of the fluid storage receptacle is thus permitted, such that fluid from the fluid storage receptacle can pass through the fluid channel 5 in the piercing mandrel D into the drip chamber 1, without pressure differences caused by lack of ventilation of the fluid storage receptacle leading to blockage of the stream of fluid.

Should fluid also accidentally pass through the first channel portion 6 of the ventilation channel 5a from the fluid storage receptacle in the direction of the second channel portion 7, a corresponding stream of fluid presses in the opposite direction, from below, against an outer face of the bottom of the membrane body 12. The slit 13 is shaped in such a way that, in conjunction with the suitably configured elastic deformability of the membrane body 12, the slit 13 remains closed when such fluid pressure acts from the direction of the underside of the membrane body 12.

What is claimed:

1. A piercing part for a medical infusion system, the piercing part comprising a housing which has a piercing mandrel and which has a fluid channel and also a ventilation channel, the ventilation channel comprising a first channel portion extending at least substantially parallel to the fluid channel, the ventilation channel further comprising a second channel portion which is diverted towards an outside of the housing and through a cylindrical wall inside the housing, the cylindrical wall containing an air filter element and a fluid shut-off member, the second channel portion being oriented parallel to the first channel portion, the cylindrical wall having an inner wall and forming an open region that faces towards an inside of the housing, the open region being closed by a separately produced closure part, the closure part comprising a lid with a peripheral edge region bearing with force-fit engagement against the inner wall of the cylindrical wall to seal off the second channel portion from the inside of the housing, the fluid shut-off member comprising a hollow cylinder having a cylinder wall and a cylinder axis surrounded by the cylinder wall, the cylinder axis extending longitudinally through a center of the cylinder wall, and the fluid channel defining a second axis extending longitudinally through a center of the fluid channel, the second axis being parallel to and laterally offset from the cylinder axis, with the second axis being outside of the hollow cylinder.

2. The piercing part according to claim 1, wherein the second channel portion has a channel outlet to the outside of the housing, which channel outlet is oriented parallel to the first channel portion of the ventilation channel.

3. The piercing part according to claim 1, wherein the fluid shut-off member is designed as a non-return valve.

4. The piercing part according to claim 3, wherein the non-return valve has a membrane body made of an elastomer material, the membrane body having a bell shape that comprises the cylinder wall of the fluid shut-off member.

5. The piercing part according to claim 1, wherein the closure part forms a 180° diversion between the first channel portion and the second channel portion.

6. The piercing part according to claim 1, wherein the housing, including the piercing mandrel and the channel portions of the ventilation channel, is produced in one piece from a thermoplastic material in an injection molding process.

7. The piercing part according to claim 1, wherein the fluid shut-off member is designed as a hydrophobic or oleophobic membrane.

8. A drip chamber for a medical infusion system comprising a piercing part according to claim 1.

9. The piercing part according to claim 1, wherein the inner wall of the cylindrical wall comprises support ribs, and the peripheral edge region of the lid is clamped with force-fit engagement onto the support ribs.

10. The piercing part according to claim 9, wherein the support ribs are distributed about a circumference of the inner wall.

11. A piercing part for a medical infusion system, the piercing part comprising a housing which has a piercing mandrel and which has a fluid channel and also a ventilation channel with a first channel portion extending at least substantially parallel to the fluid channel and with a second channel portion which is diverted towards an outside of the housing and to which an air filter element and a fluid shut-off member are assigned, the second channel portion in the housing oriented parallel to the first channel portion and open towards an inside of the housing, and in that an open region of the second channel portion is closed by a separately produced closure part, the second channel portion comprising a channel outlet to an outside of the housing, the fluid shut-off member comprising a non-return valve having a membrane body, the fluid shut-off member comprising a non-return valve having a membrane body, the fluid shut-off member comprising a hollow cylinder having a cylinder wall and a cylinder axis surrounded by the cylinder wall, the cylinder axis extending longitudinally through a center of the cylinder wall, the fluid channel defining a second axis extending longitudinally through a center of the fluid channel, the second axis being parallel to and laterally offset form the cylinder axis, with the second axis being outside of the hollow cylinder, the membrane body having a wall comprising a first end and a second end opposite the first end, the second end having an elastically deformable bottom and an opening extending along a circumference of the membrane body in a radial plane above the bottom, the wall forming a hinge in the radial plane that allows the bottom to pivot relative to the wall to an open position in which the opening connects the second channel portion and the first channel portion in fluid communication, the open position of the bottom allowing an air stream to flow from outside the housing, through the second channel portion and into the first channel portion to equalize pressure when the piercing mandrel is pushed into a fluid storage receptacle.

\* \* \* \* \*